US008557836B2

(12) United States Patent
DeGrado et al.

(10) Patent No.: US 8,557,836 B2
(45) Date of Patent: Oct. 15, 2013

(54) SPIRO-PIPERIDINE INHIBITORS

(75) Inventors: William F. DeGrado, Media, PA (US); Jun Wang, Philadelphia, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 484 days.

(21) Appl. No.: 12/545,501

(22) Filed: Aug. 21, 2009

(65) Prior Publication Data
US 2010/0069420 A1 Mar. 18, 2010

Related U.S. Application Data

(60) Provisional application No. 61/097,474, filed on Sep. 16, 2008.

(51) Int. Cl.
*A61K 31/438* (2006.01)
*A61K 31/4465* (2006.01)
*C07D 211/08* (2006.01)
*C07D 401/04* (2006.01)
*C07D 413/04* (2006.01)

(52) U.S. Cl.
USPC .............. 514/278; 546/16; 546/184; 514/315

(58) Field of Classification Search
USPC ............................. 514/278, 315; 546/16, 184
See application file for complete search history.

(56) References Cited

U.S. PATENT DOCUMENTS

| | | | |
|---|---|---|---|
| 3,328,251 A | 6/1967 | Smith | |
| 3,567,829 A | 3/1971 | Gagneux | |
| 4,005,224 A | 1/1977 | Tankersley | |
| 6,117,880 A | 9/2000 | Guo et al. | |
| 7,145,037 B2 | 12/2006 | Makovec et al. | |
| 7,951,816 B2 * | 5/2011 | Kokubo et al. ............... | 514/278 |
| 2008/0108050 A1 | 5/2008 | Montelione et al. | |
| 2008/0293685 A1 | 11/2008 | Kong et al. | |
| 2010/0063080 A1 * | 3/2010 | Press et al. .................... | 514/274 |
| 2011/0065762 A1 | 3/2011 | Wang et al. | |
| 2011/0065766 A1 | 3/2011 | Wang et al. | |
| 2011/0236881 A1 | 9/2011 | Degrado et al. | |
| 2011/0288111 A1 | 11/2011 | Degrado et al. | |
| 2011/0294785 A1 | 12/2011 | Degrado et al. | |

FOREIGN PATENT DOCUMENTS

| | | | |
|---|---|---|---|
| WO | WO 99/22735 | | 5/1999 |
| WO | WO2006/022454 | * | 3/2006 |
| WO | WO 2007/136737 | | 11/2007 |
| WO | WO 2010/019712 | | 2/2010 |
| WO | WO 2010/033339 | | 3/2010 |
| WO | WO 2010/033340 | | 3/2010 |
| WO | WO 2011/022191 | | 2/2011 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta et al., Abstract, Vippagunta, Sudha R. "Crystalline Solids." Advanced Drug Delivery Reviews 48(2001): 3-26.*
Wareing et al. (viral immunology, vol. 20, 2007, pp. 369-377).*
Wang et al (J Am Chem Soc 131:8066-8076, 2009).*
Thiel (Nature Biotechnol 2:513-519, 2004).*
Anderson (Chem and Biol 10:787-797, 2003).*
Abdel-Magid et al., "Reductive Amination of Aldehydes and Ketones with Sodium Triacetoxyborohydride. Studies on Direct and Indirect Reductive Amination Procedures", J. Org. Chem., May 31, 1996, 61(11), 3849-3862.
Betakova et al., "Influence of residue 44 on the activity of the M2 proton channel of influenza A virus", J. Gen. Virol., Jan. 2005, 86(Part 1), 181-184.
Bright et al., "Adamantane resistance among influenza Aviruses isolated early during the 2005-2006 influenza season in the United States", J. Am. Med. Assoc., Feb. 22, 2006, 295(8), 891-894.
Deyde et al., "Surveillance of resistance to adamantanes among influenza A(H3N2) and A(H1N1) viruses isolated worldwide", J. Infect. Dis., Jul. 15, 2007: Epub Jun. 7, 2007, 196(2), 249-257.
Flaugh et al., "Acid-catalyzed annelation of α-alkylaldehydes and α,β-unsaturated ketones. A one-pot synthesis of 4,4-dimethyl-2-cyclohexen-1-one", J. Org. Chem., Dec. 1980, 45(26), 5399-5400.
GenBank Accession No. AAO46668, "Membrane ion channel M2 [Influenza A virus (A/Hong Kong/16/1968(H3N2))]", May 31, 2005.
Grambas et al., "Influence of amantadine resistance mutations on the pH regulatory function of the M2 protein of influenza A viruses", Virology, Dec. 1992, 191(2), 541-549.
Hayden F.G., "Antiviral Resistance in Influenza Viruses —Implications for Management and Pandemic Response", N. Enj. J. Med., Feb. 23, 2006, 354(8), 785-788.
Jing et al., "Functional studies indicate amantadine binds to the pore of the influenza A virus M2 proton-selective ion channel", PNAS USA, Aug. 5, 2008, 105(31), 10967-10972.
Kurtz et al., "Growth impairment resulting from expression of influenza virus M2 protein in *Saccharomyces cerevisiae*: identification of a novel inhibitor of influenza virus", Antimicrob Agents Chemother., Oct. 1995, 39(10), 2204-2209.
Schnell et sl., "Structure and mechanism of the M2 proton channel of influenza A virus", Nature, Jan. 31, 2008, 451(7178), 591-595.

(Continued)

*Primary Examiner* — Savitha Rao
(74) *Attorney, Agent, or Firm* — Woodcock Washburn, LLP

(57) ABSTRACT

Provided are compounds that are capable of modulating the activity of the influenza A virus via interaction with the M2 transmembrane protein. Also provided are methods for treating an influenza A-affected disease state or infection comprising administering a composition comprising one or more compounds that have been identified as being capable of interaction with the M2 protein.

8 Claims, No Drawings

(56) References Cited

OTHER PUBLICATIONS

Tu et al., "Characterization of inhibition of M2 ion channel activity by BL-1743, an inhibitor of influenza A virus", J. Virol., Jul. 1996, 70(7), 4246-4252.
Turner et al., "A facile route to imidazol-4-yl anions and their reaction with carbonyl compounds", J. Org. Chem., Sep. 1991, 56(20), 5739-5740.
Venkataraman et al., "Chemical rescue of histidine selectivity filter mutants of the M2 ion channel of influenza A virus", J. Biol. Chem., Jun. 3, 2005, Epub: Mar. 22, 2005, 280(22), 21463-21472.
Wang et al., "Discovery of spiro-piperidine inhibitors and their modulation of the dynamics of the M2 proton channel from influenza A virus", J. Am. Chem. Soc., Jun. 17, 2009; Epub Mar. 26, 2009, 131(23), 8066-8076.
Winum et al, "N-(tert-butoxycarbonyl)-N[4-(dimethylazaniumylidene)-1,4-dihydropyridin-1-ylsulfonyl]azanide: a new sulfamyolating agent. Structure and reactivity toward amines", Org. lett., Jul. 12, 2001, 3(14), 2241-2243.
Yi et al., "A secondary gate as a mechanism for inhibition of the M2 proton channel by amantadine", J. Phys. Chem. B., Jul. 10, 2008; Epub May 14, 2008, 112(27), 7977-7799.
Acharya, et al., "Influenza A Virus Employs Water Clusters to Sequester Charge in a Biological Membrane", Submitted to Science on Jun. 9, 2009, 1-41.
Adcock et al., "Transmission of Polar Substituent Effects in the Adamantane Ring System as Monitored by 19F NMR," Magn. Reson. Chem., Mar. 1998, 36(3), 181-195.
Balannik, et al., "Design and pharmacological characterization of inhibitors of amantadine-resistant mutants of the M2 ion channel of influenza A virus", Biochemistry, Dec. 22, 2009, 48(50), 11872-11882.
Breslau, et al., "The Synthesis and Evaluation of New α-Hydrogen Nitroxides for 'Living' Free Radical Polymerization", Synthesis-Stuttgart, Jun. 2005, 2005(9), 1496-1506.
Bright et al., "Incidence of adamantane resistance among influenza A (H3N2) viruses isolated worldwide from 1994 to 2005: a cause for concern", Lancet, Oct. 2005, 366(9492), 1175-1181.
Chang et al., "Membrane permeabilization by small hydrophobic nonstructural proteins of Japanese Encephalitis virus", J. of Virology, Aug. 1999, 73(8), 6257-6264.
Geluk, et al., "Hydride transfer reactions of the adamantyl cation (IV): Synthesis of 1,4- and 2,6-substituted adamantanes by oxidation with sulfuric acid", Recueil des Travaux Chimiques des Pays-Bas, 1971, 90(5), 516-520.
Gonzalez et al., "Viroporins", FEBS Letters, Sep. 18, 2003, 552(1), 28-34.
Greene et al., "Protective Groups in Organic Synthesis", Wiley & Sons $2^{nd}$ edition, 1991, 1-405.
Han et al., "Biochemical and functional characterization of the Ebola virus VP24 protein: Implications for a role in virus assembly and budding", J. of Virology, Feb. 2003, 77(3), 1793-1800.
Han et al., "The NS3 protein of Bluetongue virus exhibits viroporin-like properties", J.of Biol. Chem., Oct. 8, 2004, 279(41), 43092-43097.
Hayden, et al., "Plaque inhibition assay for drug susceptibility testing on Influenza viruses", Antimicrobial Agents and Chemotherapy, May 1980, 17(5), 865-870.
Higuchi et al., "Pro-drugs as novel drug delivery systems", A.C.S. Symposium Series, vol. 14, Jun. 1, 1975, 1-115.
Hu, et al., "Backbone Structure of the Amantadine-Blocked Trans-Membrane Domain M2 Proton Channel from Influenza A Virus", Biophysical Journal, Jun. 15, 2007, 92(1), 4335-4343.
Ito et al., "Evolutionary analysis of the influenza A virus M gene with comparison of the M1 and M2 proteins", J. of Virology, Oct. 1991, 65(10), 5491-5498.
Jefferson et al., "Antivirals for influenza in healthy adults: systematic review", Lancet, Jan. 2006, 367(9507), 303-313.
Kalir, et al., "2-phenyl-2-adamantanamine hydrochloride—[Tricyclo[3.3.1.13,7]decan-2- amine, 2-phenyl, hydrochloride]", Organic Syntheses, 1981, 60, 104-108.

Khan et al., "Biological and Chemical Terrorism: Strategic Plan for Preparedness and Response", Recommendations of the CDC Strategic Planning Group, MMWR, Apr. 21, 2000, 49(RR-4), 1-14.
Kiso et al., "Resistant influenza A viruses in children treated with oseltamivir: descriptive study", Lancet, Aug.-Sep. 2004, 364(9436), 759-765.
Kolocouris et al., "Design and synthesis of bioactive adamantane spiro heterocycles", Bioorganic & Med. Chem. Lett., Aug. 2007, 17(15), 4358-4362.
Kolocouris et al., "Interaction between an amantadine analogue and the transmembrane portion of the influenza A M2 protein in liposomes probed by 1H NMR spectroscopy of the ligand," J. Med. Chem., Sep. 23, 2004, 47(20), 4975-4978.
Lamb et al., "The influenza A virus M2 ion channel protein and its role in the influenza virus life cycle", E. Wimmer ed., Receptor-Mediated Virus entry into Cells, Cold Spring Harbor Press, N.Y., 1994, 65-93 (Chapter 3).
Ma, et al. "Identification of the functional core of the influenza A virus A/M2 proton-selective ion channel", PNAS, Jul. 28, 2009, 106(30), 12283-12288.
Majerski, et al., "Rearrangement of bridgehead alcohols to polycyclic ketones by fragmentation-cyclization: 4-protoadamantanone (tricyclo-[4.3.1.03,8]decan-4-one)", Organic Syntheses, 1979, 59, 147-152.
Moss, et al., "Conversion of 'obstinate' nitriles to amidines by Garigipati's reaction", Tetrahedron Letters, Nov. 27, 1995, 36(48), 8761-8764.
Nasr, et al., "Rigid Multivalent Scaffolds Based on Adamantane", J. Organic Chemistry, Feb. 1, 2008, 73(3), 1056-1060.
Okada, et al., "Protonation of Histidine and Histidine-Tryptophan Interaction in the Activation of the M2 Ion Channel from Influenza A Virus", Biochemistry, May 22, 2001, 40(20), 6053-6060.
Palandoken, et al., "A facile synthesis of (tert-alkoxy)amines", Tetrahedron Letters, Sep. 26, 2005, 46(39), 6667-6669.
Pinto, et al., "A functionally defined model for the M2 proton channel of influenza a virus suggests a mechanism for its ion selectivity", PNAS, Oct. 14, 1997, 94(21), 11301-11306.
Ramaiah, et al., "1-Trifluoromethyl-1-Cyclohexanol-[Cyclohexanol, 1-(trifluoromethyl)-]", Organic Syntheses, 1995, 72, 232-240.
Remington's Pharmaceutical Sciences, 17th edition, Mack Publishing Company, Easton, PA, 1985, 1418-1419.
Rohde et al., "Discovery and metabolic stabilization of potent and selective 2-amino-N-(adamant-2-yl) acetamide 11beta-hydroxysteroid dehydrogenase type 1 inhibitors", Journal of Med. Chem., Jan. 2007, 50(1), 149-164.
Schulz et al., "SSM-based electrophysiology", Methods, Oct. 2008, 46(2), 97-103.
Shimbo, et al., "Ion selectivity and activation of the M2 ion channel of influenza virus", Biophysical Journal, Mar. 1996, 70(3), 1335-1346.
Stouffer, et al., "Structural basis for the function and inhibition of an influenza virus proton channel", Nature, Jan. 31, 2008, 451(7178), 596-599.
Stouffer, et al., "Structural basis for the function and inhibition of an influenza virus proton channel", Nature Corrigendum, Mar. 20, 2008, 452(7185), 380.
Tian, et al., "Initial structural and dynamic characterization of the M2 protein transmembrane and amphipathic helices in lipid bilayers", Protein Science, Nov. 2003, 12(11), 2597-2605.
Van Niekerk et al., "Membrane Association of African Horsesickness Virus Nonstructural Protein NS3 Determines Its Cytotoxicity", Virology, Jan. 2001, 279(2), 499-508.
Setaki et al., "Synthesis, conformational characteristics and anti-influenza virus A activity of some 2-adamantylsubstituted azacycles," Bioorganic Chemistry, Oct. 2006, 34(5), 248-273.
Fischer et al., "204. Die Synthese von 1,3-disubstituierten Adamantanen", Helv. Chim. Acta., Sep. 29, 1976, 59(6), 1953-1962 (English Abstract Included).
Han, J., "Advances in Characterization of Pharmaceutical Hydrates", Trends in Bio/Pharmaceutical Industry, Mar. 25-29, 2006.
Stella et al., "Prodrugs: Challenges and Rewards Part 1", Biotechnology: Pharmaceutical Aspects, Springer, 2007, p. 24 of Part 1.1: A Case for Prodrugs.

(56) References Cited

OTHER PUBLICATIONS

Schnell et al., Supplementary Information, 2005, Nature, 451(31): s1-s16.

Scholtissek et al., "How to overcome resistance of influenza A viruses against adamantine derivatives", 1998, Antiviral Research, 37:83-95.

Law et al., Salt-bridge dynamics control substrate-induced conformational change in the membrane transporter GlpT, 2008, Journal of Molecular Biology, 378:828-839.

\* cited by examiner

SPIRO-PIPERIDINE INHIBITORS

CROSS REFERENCE TO RELATED APPLICATIONS

The present application claims priority to U.S. Provisional App. No. 61/097,474, filed Sep. 16, 2008, the entire contents of which are hereby incorporated in their entirety.

STATEMENT OF GOVERNMENT RIGHTS

Research leading to the disclosed invention was funded in part by the U.S. National Institutes of Health, grant numbers GM56416 (William F. DeGrado) and AI 74517 (William F. DeGrado). Accordingly, the United States Government may have certain rights in the invention described herein.

TECHNICAL FIELD

The present invention pertains to, among other things, compounds and methods for modulating the activity of the influenza virus.

BACKGROUND

The M2 protein is found in the viral envelope of influenza A virus and functions as a highly selective, pH-regulated proton channel important for the life cycle of the virus. Unlike neuraminidase inhibitors, rimantadine and amantadine are anti-viral agents capable of blocking the tetrameric M2 channel. In 2006, the CDC issued an alert instructing clinicians to avoid using M2 ion-channel inhibitors during influenza season due to the extraordinarily high frequency of amantadine resistance in influenza A isolates associated with a single point mutation in the M2 protein, S31N (Hayden F. G., *Antiviral Resistance in Influenza Viruses—Implications for Management and Pandemic Response, N Enj J Med*, 2006, 354; 8). The drug-binding site is lined by residues that are mutated in amantadine-resistant viruses. Grambas, S., Bennett, M. S. & Hay, A. J. *Influence of amantadine resistance mutations on the pH regulatory function of the M2 protein of influenza A viruses. Virology* 191, 541-549 (1992); Bright, R. A., Shay, D. K., Shu, B., Cox, N. J. & Klimov, A. I. *Adamantane resistance among influenza A viruses isolated early during the 2005-2006 influenza season in the United States. J. Am. Med. Assoc.* 295, 891-894 (2006). Recently, it has been reported that resistance to rimantadine and amantadine in humans, birds and pigs has reached more than 90%, casting into doubt the continued ability of these drugs alone to satisfy the need for treatment of influenza (Deyde, V. M. et al. *Surveillance of resistance to adamantanes among influenza A(H3N2) and A(H1N1) viruses isolated worldwide. J. Infect. Dis.* 196, 249-257 (2007)).

Previous studies have suggested that BL-1743 (3-(4,5-Dihydro-1H-imidazol-2-yl)-3-aza-spiro[5.5]undecane) interacts differently with the M2 proton channel as compared with amantadine, but have found that the majority of isolated influenza viruses that are amantadine-resistant are also resistant to BL-1743. Tu Q, et al., *Characterization of inhibition of M2 ion channel activity by BL-1743, an inhibitor of influenza A virus, J Virol.* 1996 July; 70(7):4246-52. For example, Tu Q, et al. found that mutations known to confer amantadine resistance at M2 residues 27, 30, 31, and 34, all within the M2 transmembrane domain, also induce "complete" resistance to BL-1743. Id. The publication by Tu Q, et al. concluded that "the overlapping spectra of amantadine and BL-1743 resistance mutations and the higher apparent $K_i$ . . . do not indicate that BL-1743 should replace the use of amantadine (or rimantadine) for the prophylaxis or treatment of influenza virus infections in humans." Id. See also Kurtz, et al., *Growth impairment resulting from expression of influenza virus M2 protein in Saccharomyces cerevisiae: identification of a novel inhibitor of influenza virus. Antimicrob Agents Chemother.* 1995 October; 39(10):2204-9 ("BL-1743 does not produce an additive effect on M2 inhibition, suggesting that these two compounds interact with similar sites in the M2 protein . . . . Thus, BL-1743 appears to represent a novel structure with an antiviral profile similar to that of amantadine.").

SUMMARY

In one aspect of the present invention, provided are compounds having the formula (I):

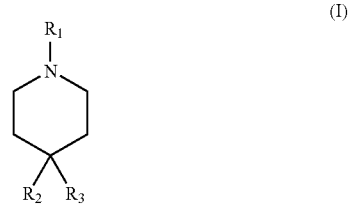

(I)

wherein $R_1$ is hydrogen or aralkyl;

$R_2$ and $R_3$ are each independently $C_2$-$C_4$ alkyl;

or, $R_2$ and $R_3$ taken together along with the carbon atom to which they are both attached form a 6-membered carbocyclic ring;

or a stereoisomer, partial stereoisomer, prodrug, pharmaceutically acceptable salt, hydrate, solvate, acid hydrate, or N-oxide thereof.

In other aspects, provided are methods treating an influenza A virus-affected disease state or infection comprising the step of administering to a subject in need thereof a composition comprising a compound of formula (I) as described above.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. Furthermore, when indicating that a certain chemical moiety "may be" X, Y, or Z, it is not intended by such usage to exclude other choices for the moiety; for example, a statement to the effect that $R_1$ "may be alkyl, aryl, or amino" does not exclude other choices for $R_1$, such as halo, aralkyl, and the like.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." In another example, when a listing of possible substituents including "hydrogen, alkyl, and aryl" is provided, the recited listing may be construed as including situations whereby any of "hydrogen, alkyl, and aryl" is negatively excluded; thus, a recitation of "hydrogen, alkyl, and aryl" may be construed as "hydrogen and aryl, but not alkyl", or simply "wherein the substituent is not alkyl".

Protective groups are abbreviated according to the system disclosed in Greene, T. W. and Wuts, P. G. M, *Protective Groups in Organic Synthesis* 2d. Ed., Wiley & Sons, 1991, which is incorporated in its entirety herein. For example, "CBZ" or "Cbz" or "Z" stands for carbobenzyloxy or benzyloxycarbonyl, "Boc" or "BOC" represents t-butoxycarbonyl, "Alloc" denotes allyloxycarbonyl, Bz means benzoyl, and "Fmoc" stands for 9-fluorenylmethoxycarbonyl.

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "μg" means microgram(s), "eq" means equivalent(s), "h" means hour(s), "μL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Where appropriate, "alkyl" can mean "alkylene"; for example, if X is —$R_1R_2$, and $R_1$ is said to be "alkyl", then "alkyl" may correctly be interpreted to mean "alkylene".

"Amino" refers to —$NH_2$ and may include one or more substituents that replace hydrogen.

As used herein, "aryl", "arene", and "aromatic" each refer to an optionally substituted, saturated or unsaturated, monocyclic, polycyclic, or other homo- or heterocyclic aromatic ring system having from about 3 to about 50 ring members (and all combinations and subcombinations of ranges and specific numbers of carbon atoms therein), with from about 5 to about 10 ring atom members being preferred. Such moieties encompass (include) "heteroaryl" and "heteroarene" as defined infra. Where appropriate, "aryl" can mean "arene"; for example, if X is —$R_1R_2$, and $R_1$ is said to be "aryl", then "aryl" may correctly be interpreted to mean "arene".

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

As used herein, "aralkyl" refers to alkyl radicals bearing one or more aryl substituents and having from about 4 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkylamido" refers to alkyl-CH(=O)NH—, wherein alkyl is as previously described. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-$SO_2$—, wherein alkyl is as previously defined.

As used herein, "alkylene" refers to an optionally branched or substituted bivalent alkyl radical having the general formula —$(CH_2)_n$—, where n is 1 to 10. Non-limiting examples include methylene, trimethylene, pentamethylene, and hexamethylene.

As used herein, "heteroaryl" or "heteroarene" refers to an aryl radical wherein in at least one of the rings, one or more of the carbon atom ring members is independently replaced by a heteroatom group selected from the group consisting of S, O, N, and NH, wherein aryl is as previously defined. Heteroaryl/heteroarene groups having a total of from about 3 to about 14 carbon atom ring members and heteroatom ring members are preferred. Likewise, a "heterocyclic ring" is an aryl radical wherein one or more of the carbon atom ring members may be (but are not necessarily) independently replaced by a heteroatom group selected from the group consisting of S, O, N, and NH. Heterocyclic rings having a total from about 3 to 14 ring members and heteroatom ring members are preferred, but not necessarily present; for example, "heterocyclohexyl" may be a six-membered aryl radical with or without a heteroatom group.

"Halo" and "halogen" each refers to a fluoro, chloro, bromo, or iodo moiety, with fluoro, chloro, or bromo being preferred.

"Haloalkyl" signifies halo-alkyl- wherein alkyl and halo, respectively, are as previously described.

The phrase reading "[moiety] is absent" means that the substituents to which the moiety is attached may be directly attached to each other.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), oxo (=O), carboxy (—COOH), —O—C(=O)R", —C(=O)R", —OR", —C(=O)OR", -(alkylene)-C(=O)—OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", —S(=O)R", —S(=O)$_2$R", —S(=O)$_2$NH$_2$, —S(=O)$_2$NHR", —S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula R.H$_2$O, where R is a compound of the invention. A given compound may form more than one hydrate including, for example, monohydrates (R.H$_2$O) or polyhydrates (R.nH$_2$O wherein n is an integer >1) including, for example, dihydrates (R.2H$_2$O), trihydrates (R.3H$_2$O), and the like, or hemihydrates, such as, for example, R.n$_{/2}$H$_2$O, R.n$_{/3}$H$_2$O, R.n$_{/4}$H$_2$O and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer >1) including, for example, disolvates (R.2(solvent)), trisolvates (R.3(solvent)), and the like, or hemisolvates, such as, for example, R.n$_{1/2}$(solvent), R.n$_{1/3}$(solvent), R.n$_{1/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Subject" or "patient" refers to an embryonic, immature, or adult animal, including the human species, that is treatable with the compositions, and/or methods of the present invention.

It has presently been discovered that certain derivatives of spiro-piperidine may be useful for the modulation of the dynamics of the M2 proton channel of the influenza A virus. In one aspect there are provided compounds having the formula (I):

(I)

wherein $R_1$ is hydrogen or aralkyl;

$R_2$ and $R_3$ are each independently $C_2$-$C_4$ alkyl;

or, $R_2$ and $R_3$ taken together along with the carbon atom to which they are both attached form a 6-membered carbocyclic ring;

or a stereoisomer, partial stereoisomer, prodrug, pharmaceutically acceptable salt, hydrate, solvate, acid hydrate, or N-oxide thereof.

With respect to the present compounds, $R_2$ and $R_3$ may be taken together along with the carbon atom to which they are both attached to form cyclohexane. In such instances, $R_1$ may be aralkyl. For example, $R_1$ may be —$CH_2$-aryl, such as —$CH_2$-cyclopropyl, —$CH_2$-cyclopentyl, —$CH_2$-(3-thiopheneyl), —$CH_2$-(1-Methyl-1H-pyrazol-4-yl), —$CH_2$-(5-Methyl-isoxazol-3-yl), —$CH_2$-(5-pyridinyl), —$CH_2$-(5-1H-imidazolyl), or —$CH_2$-(2-1H-imidazolyl).

With respect to other embodiments of the present compounds, $R_1$ is hydrogen, and $R_2$ and $R_3$ are each $C_2$-$C_4$ alkyl. For example, $R_2$ and $R_3$ may each independently be ethyl, propyl, or butyl. An exemplary compound of this variety include 4-methyl-4-ethyl-piperidinium chloride.

The compounds employed in the present invention may exist in prodrug form. As used herein, "prodrug" is intended to include any covalently bonded carriers which release the active parent drug, for example, as according to the formulas or compounds employed in the methods of the present invention in vivo when such prodrug is administered to a subject. Since prodrugs are known to enhance numerous desirable qualities of pharmaceuticals (e.g., solubility, bioavailability, manufacturing, etc.) the compounds of the present invention may, if desired, be delivered in prodrug form. Thus, the present invention contemplates methods of delivering prodrugs. Prodrugs of the compounds employed in the present invention, for example, according to formula (I), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed, Wiley & Sons, 1991.

In a further aspect, the invention relates to pharmaceutical compositions comprising a compound according to formula (I) and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety.

Also provided are methods for treating an influenza A virus-affected disease state or infection comprising the step of administering to a subject in need thereof a composition comprising a compound of formula (I):

$$\text{(I)}$$

wherein $R_1$ is hydrogen or aralkyl;

$R_2$ and $R_3$ are each independently $C_2$-$C_4$ alkyl;

or, $R_2$ and $R_3$ taken together along with the carbon atom to which they are both attached form a 6-membered carbocyclic ring;

or a stereoisomer, partial stereoisomer, prodrug, pharmaceutically acceptable salt, hydrate, solvate, acid hydrate, or N-oxide thereof.

The influenza A virus-affected disease state or infection may comprise any condition that arises as a direct or indirect result of the presence of influenza A virus. For example, the influenza A virus-affected disease state may comprise influenza (flu), pneumonia, bronchitis, sinus infection, or ear infection, among other conditions. The disease state or infection may arise as a direct or indirect result of the presence of wild-type influenza A virus, or may arise as a direct or indirect result of the presence of a mutant version of the influenza A virus, or may arise as a direct or indirect result of the presence of both a wild-type influenza A virus and a mutant version of the influenza A virus. Thus, in accordance with the present methods, the influenza A virus may be wild-type or may be a mutant virus. The mutant virus may comprise an influenza A virus having the V27G mutation, the V27II mutation, the V27T mutation, the V27S mutation, or the V27A mutation; may comprise an influenza virus having the A30T mutation; may comprise an influenza virus having the S31A mutation or the S31N mutation; may an influenza virus having the G34E mutation or the G34A mutation; may comprise an influenza virus having the W41L mutation or the W41Y mutation; may comprise an influenza virus having the D44N mutation or the D44H mutation; and/or may comprise an influenza virus having the R45K mutation or the R45H mutation.

With respect to the present methods, $R_2$ and $R_3$ may be taken together along with the carbon atom to which they are both attached to form cyclohexane. In such instances, $R_1$ may be aralkyl. For example, $R_1$ may be —$CH_2$-aryl, such as —$CH_2$-cyclopropyl, —$CH_2$-cyclopentyl, —$CH_2$-(3-thiopheneyl), —$CH_2$-(1-Methyl-1H-pyrazol-4-yl), —$CH_2$-(5-Methyl-isoxazol-3-yl), —$CH_2$-(5-pyridinyl), —$CH_2$-(5-1H-imidazolyl), or —$CH_2$-(2-1H-imidazolyl).

With respect to other embodiments of the present methods, $R_1$ is hydrogen, and $R_2$ and $R_3$ are each $C_2$-$C_4$ alkyl. For example, $R_2$ and $R_3$ may each independently be ethyl, propyl, or butyl. An exemplary compound of this variety include 4-methyl-4-ethyl-piperidinium chloride.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspensing/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including, for example, the compounds of formula I may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Synthesis and NMR Spectroscopy Data of Exemplary Influenza A M2 Proton Channel Inhibitors All chemicals were purchased from commercial vendors and used without further purification unless otherwise noted. 3,3-Pentamethylene glutarimide was purchased from Bosche, N.J. $^1$H NMR and $^{13}$C NMR spectra were recorded on a DMX-360 NMR spectrometer. Chemical shifts are reported in parts per million referenced with respect to residual solvent (CHCl$_3$=7.26 ppm and DMSO-d6=2.50 ppm) or from internal standard tetramethylsilane (TMS=0.00 ppm). The following abbreviations were used in reporting spectra: s=singlet, d=doublet, t=triplet, q=quartet, m=multiplet, dd=doublet of doublets. All reactions were carried out under N2 atmosphere, unless otherwise stated. HPLC grade solvents were used for all the reactions. Column chromatography was performed using silica gel (230-400 mesh). Low-resolution mass spectra were obtained on an LC platform from Micromass using ESI technique.

Synthesis of BL-1743 started with reduction of commercially available 3,3-pentamethylene glutarimide with LiAlH$_4$ in refluxing THF to give 3-azaspiro[5,5]undecane hydrochloride (9) in 75% yield after treatment with HCl/ether (see Scheme 1, below). Subsequent nucleophilic substitution of 2-methylthio-2-imidazoline with 9 furnished the model compound BL-1743. Reductive amination of 9 with different aldehydes using NaBH(OAc)$_3$/HCO$_2$H in dichloroethane gave 1-8 with yields of 65% to 95%. The results showed that replacements of the imidazoline ring of BL-1743 with either hydrophobic substitutions or heterocycles lacking hydrogen-bond donors (HBD) led to complete loss of potency at 100 μM, as AM2 still retained >90% activity after inhibition. In contrast, inhibitors 7 and 8 with the imidazole headgroup retain moderate inhibition. This suggests that a hydrogen-bond donor may be necessary for the inhibitory activity. Synthesis scheme 1:

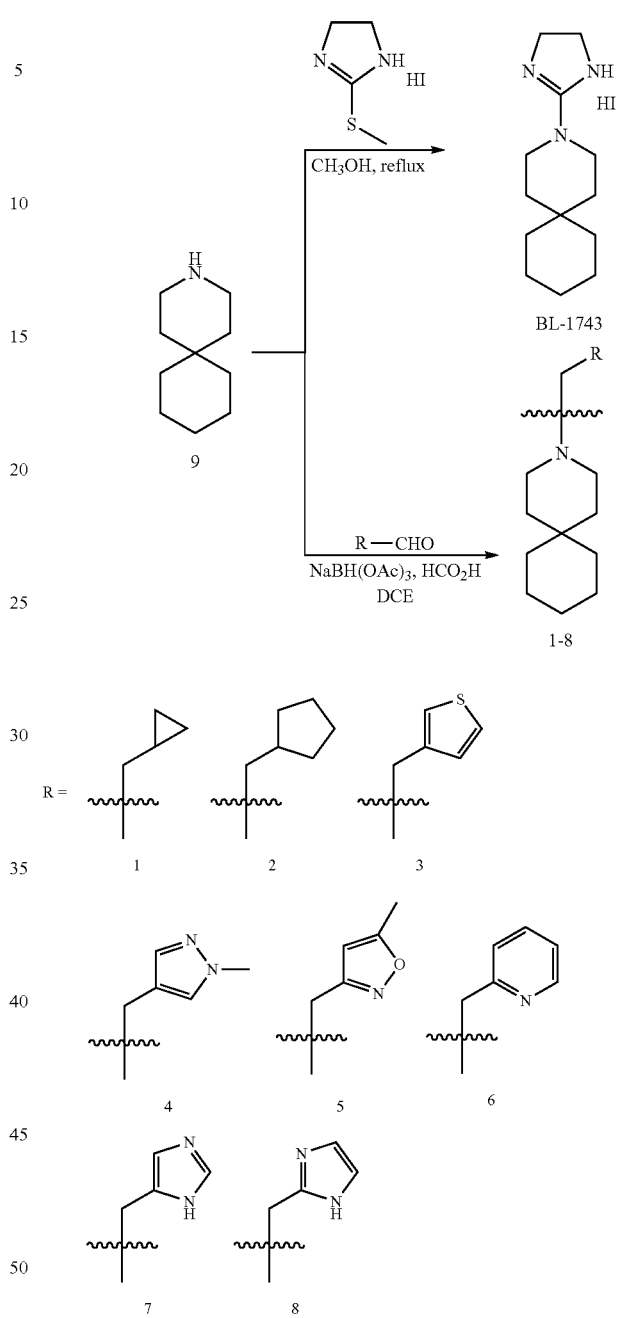

Two 4,4-disubstituted piperidines (designated below as 19 and 20) were also synthesized as follows:

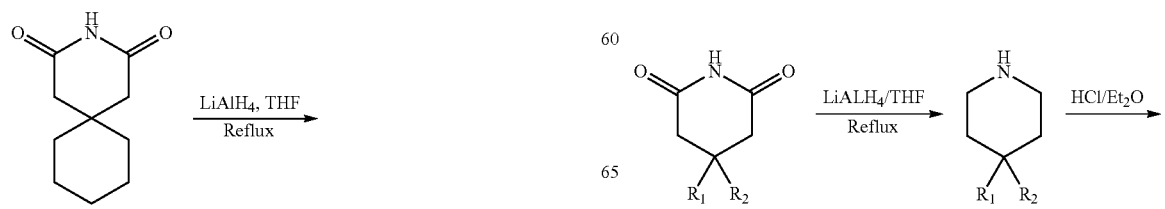

-continued

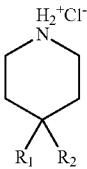

R₁ = CH₃, R₂ = CH₃   19
R₁ = CH₃, R₂ = CH₂CH₃   20

In Vitro cRNA Transcription, Heterologous Expression and Electrophysiological Recordings. The cDNA encoding to the influenza virus A/Udorn/72 AM2 protein was inserted into pGEMHJ (a gift from N.Dascal Tel-Aviv University, Israel) for the expression on *Xenopus* oocytes. Plasmid was linearized with HindIII, and capped cRNA was transcribed in vitro using T7 RNA polymerase (mMessage mMachine; Ambion, Austin, Tex.). The quality of transcripts was assessed by agarose gel electrophoresis and ethidium bromide staining and analytical UV spectroscopy. Stage V-VI *Xenopus laevis* oocytes were prepared as described in published literature. Oocytes were injected with 5-10 ng of cRNA in 50 nl/oocyte, and assayed 2-3 days later. Two electrode voltage clamp recordings were carried out using TEV-200 (Dagan, Minneapolis, Minn.) connected to DIGIDATA 1440A and pCLAMP10 (Axon Instruments, Foster City, Calif.). Oocytes were superfused with Barth's solution containing 88 mM NaCl, 1 mM KCl, 2.4 mM NaHCO₃, 0.3 mM NaNO₃, 0.71 mM CaCl₂, 0.82 mM MgCl₂ and 15 mM HEPES for pH 8.5 or 15 mM MES for pH 5.5. Currents were recorded at −20 mV. Dose-inhibition curves were usually constructed by applying 1-3 concentrations per oocyte of antagonist mixed in recording pH5.5 Barth's solution, and currents were normalized to the steady-state current obtained with pH5.5 Barth solution alone. Data were analyzed using the ORIGIN 8.0 software (OriginLab, Northampton, Mass.).

Preparation of M2 membrane samples for solid-state NMR. $^{13}$C and $^{15}$N-labeled AM2-TM (22-46) of the Udorn strain (SSDPL VVAASII GILHLIL WILDRL) was synthesized by PrimmBiotech (Cambridge, Mass.) and purified to >95%. $^{13}$C and $^{15}$N-labeled amino acids were placed at L26, A29, G34 and I35 in one sample and V27, A30, I33 and L38 in another sample.

AM2-TM was reconstituted into 1,2-dilauroyl-sn-glycero-3-phosphatidylcholine (DLPC) or 1,2-dimyristoyl-sn-glycero-3-phosphatidylcholine (DMPC) bilayers by detergent dialysis as described in published literature. The peptide structure and dynamics have been extensively characterized in both bilayers. AM2-TM was first dissolved in octyl-β-D-glucopyranoside (OG) solution, then mixed with the lipid vesicle solution at pH 7.5. OG was then removed by dialysis for 3 days. The peptide-lipid suspension was ultracentrifuged to obtain the membrane pellet. The peptide:lipid molar ratio was 1:15. 3-azaspiro[5,5]undecane was added to the membrane by either direct titration to the pellet at a peptide:drug molar ratio of 1:2, or through a 10 mM solution before ultracentrifugation. For the latter, the percent spiro-piperidine 9 remaining in the supernatant was quantified by $^1$H solution NMR to be 60%, giving a peptide: drug molar ratio of 1:8 in the membrane pellet.

Solid-state NMR spectroscopy. SSNMR experiments were carried out on Bruker wide-bore AVANCE and DSX spectrometers at 14.1 Tesla and 9.4 Tesla (Karlsruhe, Germany) using 4 mm magic-angle-spinning (MAS) probes. Radio-frequency pulse lengths were typically 5 μs for $^{13}$C and $^{15}$N and 3.5-4.0 μs for $^1$H. $^1$H TPPM or SPINAL decoupling field strengths of 60-70 kHz were applied. $^{13}$C and $^{15}$N chemical shifts were referenced, respectively, to the α-Gly C' signal at 176.49 ppm on the TMS scale and the $^{15}$N signal of N-acetyl-valine at 122.0 ppm on the liquid ammonia scale. 2D $^{13}$C—$^{13}$C correlation was carried out using the INADEQUATE sequence which better resolves sidechain methyl signals than the standard spin diffusion experiments. 2D $^{15}$N—$^{13}$C correlation was carried out using an HSQC-type sequence incorporating a REDOR train for $^{15}$N—$^{13}$C coherence transfer. The 2D spectra were measured at 243 K to freeze the peptide motion.

The numbers of scans for the 1D $^{15}$N CP spectra of the apo-, amantadine-bound and spiro-piperidine-bound AM2-TM were 3,000-6,000 at low temperatures (<263 K) and 30,000-40,000 at high temperatures (>263 K). For the 2D $^{15}$N-$^{13}$C correlation spectra, 352 scans were coadded per t₁ slice and a maximum t₁ evolution time of 8.8 ms was used, resulting in a measuring time of 21 hours for each experiment. For the 2D $^{13}$C—$^{13}$C INADEQUATE spectra, the number of scans per t₁ slice was 192 and the maximum t₁ evolution time was 6.4 ms. The measuring time was 20 hours for each experiment.

3-(4,5-dihydro-1H-imidazol-2-yl)-3-azaspiro[5,5]undecane hydroiodide (BL-1743). 3-Azaspiro[5,5]undecane (0.38 g, 2 mmol) and 2-methylthio-2-imidazoline hydroiodide (0.44 g, 1.8 mmol) was refluxing in CH₃OH overnight, concentrated in vacuo and purified by flash chromatography to give yellow oil (0.26 g, 65% yield). $^1$H NMR (360 MHz, CDCl₃) δ 8.27 (br s, 2H), 3.72 (s, 4H), 3.39 (t, J=5.83 Hz, 4H), 1.50 (t, J=5.94 Hz, 4H), 1.47-1.44 (m, 10H); $^{13}$C NMR (90 MHz, CDCl₃) δ 159.48, 43.39, 42.73, 36.02, 35.26, 30.83, 26.65, 21.61. 21.49; ESI-MS: Calculated for C₁₃H₂₄IN₃ (M−I)⁺ 222.3, Found: 222.5.

3-(cyclopropylmethyl)-3-azaspiro[5,5]undecane (1). To a solution of 3-azaspiro[5,5]undecane (0.34 g, 2.2 mmol), cyclopropanecarbaldehyde (0.14 g, 2 mmol) and NaBH(OAc)₃ (0.64 g, 3 mmol) in dichloroethane (10 mL) were added AcOH (0.12 mL, 2 mmol), the resulting suspension was stirred overnight, quenched with NaHCO₃ and extracted with CH₂Cl₂ twice, the combined organic layer was washed with brine, and dried with MgSO₄. The solution was filtered, concentrated in vacuo and purified by flash chromatography. The compound was converted to the hydrochloride by passing HCl gas into the ether solution of 3-(cyclopropylmethyl)-3-azoniaspiro[5,5]undecane at 0° C., followed by decanting the ether supernatant, the final white solid (0.39 g, 80% yield) was dried in vacuo. $^1$H NMR (360 MHz, CDCl₃) δ 2.45 (t, J=5.66 Hz, 4H), 2.23 (d, J=6.51 Hz 2H), 1.49 (t, J=5.66 Hz, 4H), 1.48-1.40 (m, 6H), 1.38-1.30 (m, 4H), 0.92-0.82 (m, 1H), 0.52-0.47 (m, 2H), 0.11-0.17 (m, 2H); $^{13}$C NMR (90 MHz, CDCl₃) δ 64.55, 49.67, 36.47, 35.46, 31.00, 27.12, 21.73, 8.74, 4.19; ESI-MS: Calculated for C₁₄H₂₅N (M+H)⁺ 208.4, Found: 208.4.

3-(cyclopentylmethyl)-3-azaspiro[5,5]undecane (2). This compound was prepared by the same procedure as described for the synthesis of 1.95% yield. $^1$H NMR (360 MHz, CDCl₃) δ 2.35 (t, J=5.56 Hz, 4H), 2.25 (d, J=7.08 Hz, 2H), 2.06-2.02 (m, 1H), 1.76-1.73 (m, 2H), 1.58-1.52 (m, 4H), 1.45 (t, J=5.56 Hz, 4H), 1.43-1.39 (m, 6H), 1.39-1.31 (m, 4H), 1.20-1.14 (m, 2H); $^{13}$C NMR (90 MHz, CDCl₃) δ 65.52, 49.93, 37.80, 36.51, 35.47, 32.08, 31.00, 27.14, 25.44, 21.74; ESI-MS: Calculated for C₁₆H₂₉N (M+H)⁺ 236.4, Found: 236.6.

3-(thiophen-3-ylmethyl)-3-azaspiro[5,5]undecane (3). This compound was prepared by the same procedure as described for the synthesis of 1.92% yield. $^1$H NMR (360 MHz, CDCl₃) δ 7.24 (d, J=4.88 Hz, 1H), 7.09 (s, 1H), 7.04 (d, J=4.88 Hz, 1H), 3.35 (s, 2H), 2.37 (t, J=5.52 Hz, 4H), 1.46 (t, J=5.52 Hz, 4H), 1.37-1.34 (m, 6H), 1.30-1.26 (m, 4H); $^{13}$C NMR (90 MHz, CDCl$_3$) δ 129.02, 125.39, 123.11, 58.14, 49.37, 36.77, 36.35, 30.92, 27.08, 21.72; ESI-MS: Calculated for C$_{15}$H$_{23}$NS (M+H)$^+$ 250.4, Found: 250.4.

3-((1-methyl-1H-pyrazol-4-yl)methyl)-3-azaspiro[5,5] undecane (4). This compound was prepared by the same procedure as described for the synthesis of 1.82% yield. $^1$H NMR (360 MHz, CDCl$_3$) δ 7.93 (s, 1H), 7.28 (s, 1H), 3.87 (s, 3H), 3.41 (s, 2H), 2.38 (t, J=5.38 Hz, 4H), 1.46 (t, J=5.38 Hz, 4H), 1.39-1.34 (m, 6H), 1.30-1.24 (m, 4H); $^{13}$C NMR (90 MHz, CDCl$_3$) δ 141.15, 140.30, 130.18, 52.93, 48.97, 39.03, 36.29, 35.45, 30.90, 27.05, 21.70; ESI-MS: Calculated for C$_{15}$H$_{25}$N$_3$(M+H)$^+$ 248.4, Found: 248.6.

3-(3-azaspiro[5,5]undecan-3-ylmethyl)-5-methylisoxazole (5). This compound was prepared by the same procedure as described for the synthesis of 1.75% yield. $^1$H NMR (360 MHz, CDCl$_3$) δ 6.00 (s, 1H), 3.54 (s, 2H), 2.41 (t, J=5.73, 4H), 2.39 (s, 3H), 1.46 (t, J=5.73 Hz, 4H), 1.39-1.35 (m, 6H), 1.30-1.25 (m, 4H); $^{13}$C NMR (90 MHz, CDCl$_3$) δ 169.41, 161.90, 102.05, 53.94, 49.49, 36.74, 30.75, 27.05, 21.68, 12.47; ESI-MS: Calculated for C$_{15}$H$_{24}$N$_2$O (M+H)$^+$ 249.4, Found: 249.6.

3-(pyridin-2-ylmethyl)-3-azaspiro[5,5]undecane (6). This compound was prepared by the same procedure as described for the synthesis of 1.84% yield. $^1$H NMR (360 MHz, CDCl$_3$) δ 8.56 (d, J=4.8 Hz, 1H), 7.63 (td, J=7.6, 1.6 Hz, 1H), 7.40 (d, J=7.2 Hz, 1H), 7.15-7.13 (m, 1H), 3.65 (s, 2H), 2.44 (t, J=5.58 Hz, 4H), 1.48 (t, J=5.58 Hz, 4H), 1.39-1.36 (m, 6H), 1.30-1.25 (m, 4H); $^{13}$C NMR (90 MHz, CDCl$_3$) δ 149.36, 136.47, 130.58, 123.42, 122.03, 65.32, 49.79, 36.44, 35.46, 30.87, 27.10, 21.72; ESI-MS: Calculated for C$_{16}$H$_{24}$N$_2$ (M+H)$^+$ 245.4, Found: 245.6.

3-((1H-imidazol-4-yl)methyl)-3-azaspiro[5.5]undecane (7). The same procedure as described for synthesis 1.68% yield. $^1$H NMR (360 MHz, CD$_3$OD) δ 8.97 (s, 1H), 7.81 (s, 1H), 4.56 (s, 2H), 3.34 (br s, 4H), 1.77 (br s, 4H), 1.54-1.48 (m, 10H); $^{13}$C NMR (90 MHz, CDCl$_3$) δ 137.47, 124.34, 123.60, 50.18, 49.86, 34.31, 31.21, 27.58, 22.50; ESI-MS: Calculated for C$_{14}$H$_{23}$N$_3$ (M+HH)$^+$ 234.4, Found: 234.6.

3-((1H-imidazol-2-yl)methyl)-3-azaspiro[5.5]undecane (8). This compound was prepared by the same procedure as described for the synthesis of 1.65% yield. $^1$H NMR (360 MHz, CD$_3$OD) δ 7.51 (s, 2H), 4.55 (s, 2H), 3.22 (t, J=5.94 Hz 4H), 1.74 (t, J=6.01 Hz, 4H), 1.47-1.45 (m, 10H); $^{13}$C NMR (90 MHz, CDCl$_3$) δ 123.49, 51.45, 50.37, 34.64, 31.16, 27.62, 22.51; ESI-MS: Calculated for C$_{14}$H$_{23}$N$_3$ (M+H)$^+$ 234.4, Found: 234.6.

4,4-dimethylpiperidinium chloride (19). Synthesis of 19 was accomplished using the same procedure as described for 9.87% yield. $^1$H NMR (360 MHz, CDCl$_3$) δ 9.37 (br s, 2H), 3.15 (t, J=5.97, 4H), 1.68 (t, J=5.97, 4H), 1.04 (s, 6H), 1.56 (s, 1H); $^{13}$C NMR (90 MHz, CDCl$_3$) δ 40.64, 35.21, 28.29, 27.64; ESI-MS: Calculated for C$_7$H$_{16}$ClN (M−CL)$^+$ 114.4, Found: 114.6.

4-ethyl-4-methylpiperidinium chloride (20). Synthesis of 20 was accomplished using the same procedure as described for 9.82% yield. $^1$H NMR (360 MHz, CDCl$_3$) δ 9.38 (br s, 2H), 3.19-3.09 (m, 4H), 1.77-1.73 (m, 2H), 1.71-1.62 (m, 2H), 1.37 (q, J=7.34 Hz, 2H), 0.97 (s, 3H), 0.85 (t, J=7.45 Hz, 2H); $^{13}$C NMR (90 MHz, CDCl$_3$) δ 40.37, 33.41, 33.24, 30.70, 22.88, 7.52; ESI-MS: Calculated for C$_8$H$_{18}$ClN (M−Cl)$^+$ 128.2, Found: 128.4.

Example 2

Structure-Activity Relationship (SAR) of Exemplary Influenza A M2 Proton Channel Inhibitors The activity of the inhibitors were measured using the TEV technique with full length Udorn AM2 protein in the *Xenopus* oocytes membrane. All inhibitors were initially tested at 100 µM; those that inhibited the AM2 channel activity by more than 70% (less than 30% remaining activity) were chosen for measurement of their IC$_{50}$.

Table 1, below, provides AM2 channel proton conductivity after applying 100 µM inhibitors with cyclic hydrophobic and heterocyclic head groups.

TABLE 1

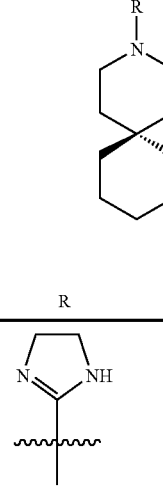

| Compound | R | AM2 Remaining Activity After 100 µM inhibition | IC$_{50}$ (µM) |
|---|---|---|---|
| BL-1743 | 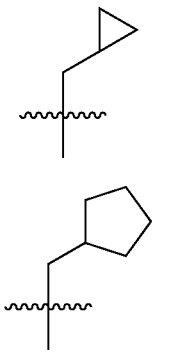 | 25% | 45.3 ± 3.9 |
| 1 | 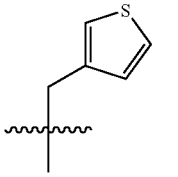 | 100% | n/a |
| 2 | 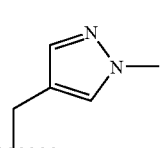 | 100% | n/a |
| 3 | 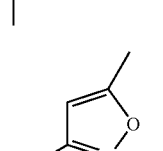 | 90% | n/a |
| 4 |  | 100% | n/a |
| 5 |  | 100% | n/a |

TABLE 1-continued

| Compound | R | AM2 Remaining Activity After 100 μM inhibition | $IC_{50}$ (μM) |
|---|---|---|---|
| 6 | 2-pyridylmethyl | 100% | n/a |
| 7 | (1H-imidazol-4-yl)methyl | 70% | n/a |
| 8 | (1H-imidazol-2-yl)methyl | 49% | n/a |

Table 2, below, provides AM2 channel proton conductivity after respectively applying 100 μM of two 4,4-disubstituted piperidines (19 and 20):

TABLE 2

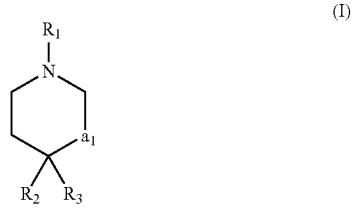

| Compound | $R_1, R_2$ | AM2 Remaining Activity After 100 μM inhibition |
|---|---|---|
| 19 | $CH_3, CH_3$ | 75% |
| 20 | $CH_3, CH_2CH_3$ | 87% |

Additional information regarding the present invention can be found in Wang J, Cady S D, Balannik V, Pinto L H, DeGrado W F, Hong M *Discovery of spiro-piperidine inhibitors and their modulation of the dynamics of the M2 proton channel from influenza A virus*. *J Am Chem Soc*. 2009 Jun. 17; 131(23):8066-76, which is hereby incorporated by reference in its entirety.

What is claimed:

1. A method for treating infection by influenza A virus or an influenza A virus-affected disease state comprising the step of administering to a subject in need thereof a composition comprising a compound of formula (I):

(I)

wherein $R_1$ is hydrogen, alkyl, aralkyl, cycloalkyl-alkyl $a_1$ is —$CH_2$—;

$R_2$ and $R_3$ are each independently $C_2$-$C_4$ alkyl, or, $R_2$ and $R_3$ taken together along with the carbon atom to which they are both attached form a 6 membered carbocyclic ring or a stereoisomer or pharmaceutically acceptable salt thereof.

2. The method according to claim 1 wherein said influenza A virus-affected disease state or infection comprises influenza (flu).

3. The method according to claim 1 wherein said influenza A virus-affected disease state or infection comprises one or more of pneumonia, bronchitis, sinus infection, and ear infection.

4. The method according to claim 1 said composition additionally comprises a pharmaceutically acceptable carrier, diluent, or excipient.

5. The method according to claim 1 wherein said influenza A virus is a wild-type virus.

6. The method according to claim 1 wherein said influenza A virus is a mutant.

7. The method according to claim 1 wherein $R_2$ and $R_3$ taken together along with the carbon atom to which they are both attached form cyclohexane.

8. The method according to claim 1 wherein $R_1$ is hydrogen, and $R_2$ and $R_3$ are each $C_2$-$C_4$ alkyl.

* * * * *